(12) United States Patent
Bryan et al.

(10) Patent No.: US 8,535,413 B2
(45) Date of Patent: Sep. 17, 2013

(54) INTEGRATED MECHANICAL VAPOR RECOMPRESSION (MVR) AND MEMBRANE VAPOR PERMEATION PROCESS FOR ETHANOL RECOVERY (ETHANOL DEHYDRATION) FROM FERMENTATION BROTH

(75) Inventors: Paul Bryan, Pinole, CA (US); Oluwasijibomi Okeowo, Clayton, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 260 days.

(21) Appl. No.: 12/972,098

(22) Filed: Dec. 17, 2010

(65) Prior Publication Data

US 2011/0318800 A1    Dec. 29, 2011

Related U.S. Application Data

(60) Provisional application No. 61/290,407, filed on Dec. 28, 2009.

(51) Int. Cl.
*B01D 53/22* (2006.01)
*C12P 7/06* (2006.01)
*C12M 1/00* (2006.01)

(52) U.S. Cl.
USPC ............ 95/45; 95/43; 95/46; 95/50; 95/51; 96/4; 96/6; 96/9; 210/640; 435/161; 435/289.1; 435/297.1

(58) Field of Classification Search
USPC ............ 95/43, 45, 50, 51, 204, 46; 96/4, 96/7, 9, 351, 355, 6; 521/640, 641; 435/161, 435/163, 289.1, 297.1; 568/913; 210/640, 210/641

See application file for complete search history.

(56) References Cited

U.S. PATENT DOCUMENTS

| | | | |
|---|---|---|---|
| 4,340,446 A | 7/1982 | Crawford | |
| 4,428,799 A | 1/1984 | Standiford | |
| 5,141,861 A * | 8/1992 | Dale | 435/162 |
| 5,772,734 A * | 6/1998 | Baker et al. | 95/50 |
| 6,059,857 A * | 5/2000 | Ray et al. | 95/52 |
| 2001/0042716 A1* | 11/2001 | Iversen et al. | 210/640 |
| 2007/0031954 A1 | 2/2007 | Mairal et al. | |
| 2009/0057128 A1* | 3/2009 | Vane et al. | 203/17 |
| 2009/0117631 A1* | 5/2009 | Cote et al. | 435/161 |
| 2010/0087687 A1* | 4/2010 | Medoff | 568/840 |
| 2011/0152584 A1* | 6/2011 | Pasanen et al. | 568/916 |
| 2012/0283489 A1* | 11/2012 | Nemser et al. | 568/913 |

OTHER PUBLICATIONS

Scopes RK, vol. 7, No. 4, 1997 pp. 296-299.
Transport processes and unit operations by Christie J. Geankoplis, p. 515 Chapter 8, $3^{rd}$ Ed (1993). Prentice-Hall, Inc New Jersey USA.
Mechanical Vapor Recompression and Membrane Polishing by John Burke, presentation at the $10^{th}$ Annual Chemical Management Services Workshop in San Francisco CA (accessed online).

* cited by examiner

*Primary Examiner* — Jason M Greene
(74) *Attorney, Agent, or Firm* — A. Stephen Zavell

(57) ABSTRACT

An apparatus and process is taught for the formation of ethanol from a fermentation medium in the absence of an ethanol concentration distillation step.

9 Claims, 3 Drawing Sheets

INTEGRATED MECHANICAL VAPOR RECOMPRESSION (MVR) AND MEMBRANE VAPOR PERMEATION PROCESS FOR ETHANOL RECOVERY (ETHANOL DEHYDRATION) FROM FERMENTATION BROTH

This application claims the benefit of the filing date of the U.S. Provisional Application No. 61/290,407 filed on Dec. 28, 2009.

FIELD OF THE INVENTION

The invention relates to a process for ethanol recovery from a fermentation process. More specifically the invention relates to ethanol production process providing energy savings over conventional/traditional technologies that include a distillation step.

BACKGROUND OF THE INVENTION

The ethanol stream (broth) coming from the fermentor in a fermentation process for producing biofuel (ethanol) contains a significant amount of water and some unfermented solids. To recover fuel grade ethanol in this stream involves a water removal step (dehydrate), wherein water typically accounts for >85 wt % of the fermentation broth. The conventional process of removing water from the ethanol stream is via distillation, and the overhead stream from the rectifying column of the distillation step is sent to a molecular sieve for further dehydration to approach pure ethanol. The use of distillation for alcohol recovery is energy intensive because the heat supplied is also used to vaporize the water, thus reducing thermal efficiency. In addition, there is a limit to the degree of ethanol purity that can be achieved with conventional distillation. For example, distillation is a poor choice for separation once the ethanol-water mixture reaches the azeotropic composition (96.4 wt % ethanol). Other distillation methods, such as azeotropic distillation and extractive distillation, are applicable but they are all energy intensive processes and in most cases involve introducing additional separation steps to the process for ancillary solvent recovery which add cost to the process.

One common feature of any fermentation technology pathway is the need for ethanol recovery post-fermentation and this is currently being done using distillation. Based on ethanol production energy analysis, ethanol recovery step is reported to account for more than 45% of the total energy requirement for a given plant. It is therefore highly desirable to find alternative technologies/processes that are less energy intensive than a distillation process.

Various approaches have been or are currently being explored to find a solution to the problem of reducing the energy consumption of the ethanol recovery step in ethanol production plants. One of such approaches is the development of membrane-based processes for ethanol dehydration, e.g. pervaporation (PV) and vapor permeation (VP). Pervaporation is a separation process in which a liquid mixture is brought into contact with a semi-permeable membrane on the feed side, and the membrane selectively removes one component (mainly due to stronger affinity) to the permeate side while rejecting the other components with lower affinity to the residue or reject side. Vapor permeation is similar to pervaporation, however the feed is in vapor phase. Membrane processes are reported to consume less energy than distillation and may offer energy savings of roughly 50% depending on the membrane material's productivity and separation efficiency. Membranes also require less plant footprint than distillation processes. Membrane operations have the potential to be simpler in comparison to distillation operations. An issue with membrane processes without distillation is the need for solids removal prior to the dehydration of ethanol and pretreatment of the broth solids as contaminants can impact the performance of the membrane unit. Patent application 2007/0031954 describes an integrated process which includes multiple membranes which include a first membrane separation, followed by dephlegmation step, and another membrane separation for ethanol dehydration. A problem with this approach is the need for solids removal from the fermentation broth before the membrane separation process. The solids removal step creates additional capital investments and operating costs which increases the overall ethanol production cost.

Mechanical vapor recompression (MVR) is an approach that has not been used for ethanol dehydration MVR concepts have been reportedly used in the form of single effect evaporation for desalination of water, for concentrating black liquor in the paper industry, and for wastewater treatment. MVR is reportedly less energy intensive than distillation, and therefore an integrated process comprising a MVR unit operation and a membrane separation process should offer significant cost savings in ethanol production. In a MVR process, the vapor generated from a column or evaporator type arrangement is recompressed, to elevate the pressure and temperature, and then heat exchanged with the feed to the column or evaporator. The vapor generated in the MVR unit should be free of solids and non-volatile contaminants for ethanol—water separation. The ethanol concentration in the vapor from the MVR needs to be treated further to meet desired specifications.

DESCRIPTION OF THE INVENTION INCLUDING PREFERRED EMBODIMENTS

The invention includes the apparatus and use of an integrated process comprising a mechanical vapor recompression (MVR) unit and a membrane separation process, such as vapor permeation or pervaporation. The process of the invention reduces the energy consumption required for ethanol recovery by more than 25% and preferably by at least 50% or more to improve the overall economics of ethanol production.

Figure 1:
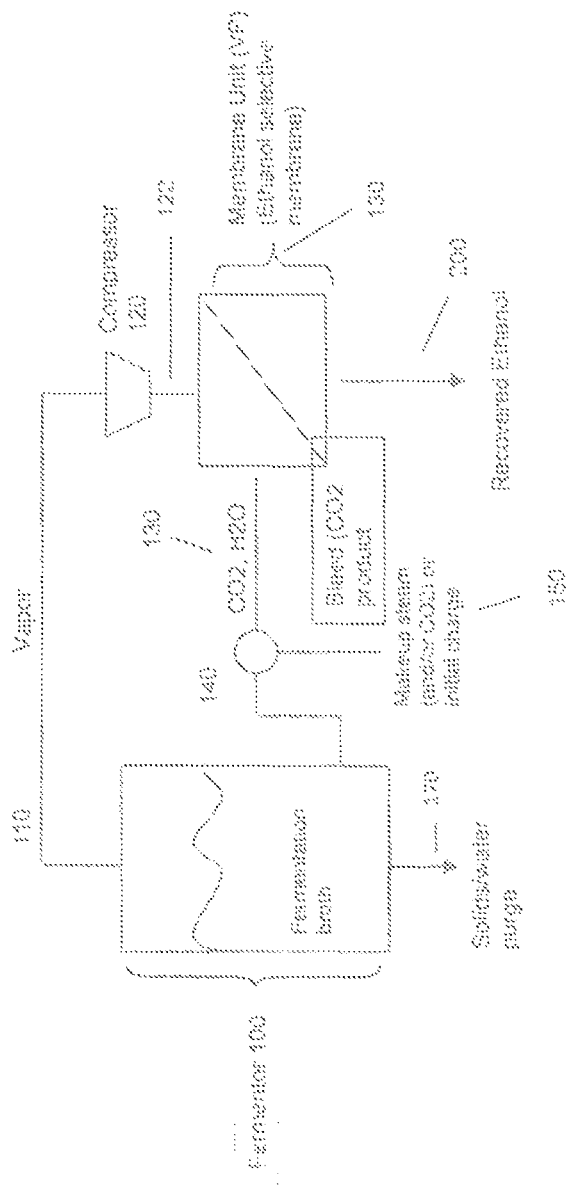
FIG. 1 illustrates a schematic of integrated MVR and membrane separation process with direct $CO_2$ and steam injection.
Figure 2:
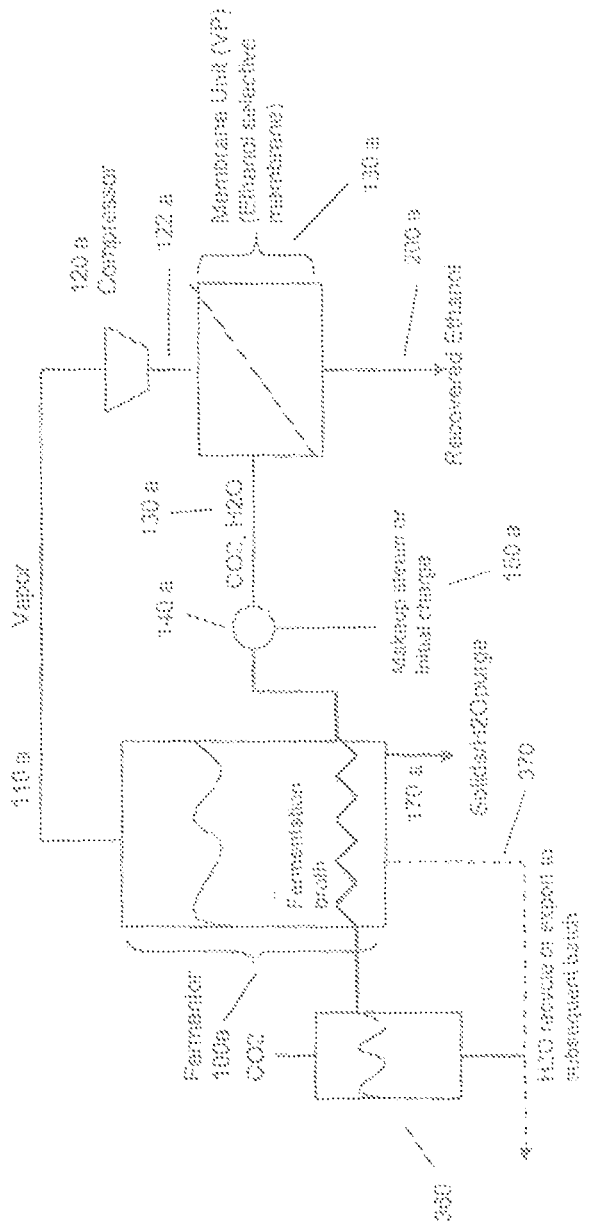
FIG. 2 illustrates a schematic of integrated MVR and membrane separation process with a $CO_2$ removal step.

A typical fermentation broth in a batch fermentor (reactor) contains >85 wt % water with the balance being ethanol, $CO_2$, and unfermented solids. The schematics of an integrated MVR and membrane process are shown in FIGS. 1 and 2. A vapor stream is generated in the fermentor by bubbling steam and $CO_2$ through the content of the fermentor. The $CO_2$-steam combination serves as a gas-lift (steam vaporizing the ethanol) for the ethanol component in the fermentor. The generated vapor (mostly steam, ethanol, and $CO_2$) is transported into the MVR unit where a hotter stream is generated by recompression. By way of an example when a the total steam rate of ~190$1b$/hr is used to for 1 wt % ethanol in a feed rate of 1000 lb/hr fermentation broth, this implies a 1.9 lb of steam for 1 lb of ethanol in the broth. Based on this, as a rough approximation, anything from 1× to 2× or at most 3× amount of ethanol in feed will be the steam requirement. The amount of steam required decreases as the ethanol concentration in the feed increases, assuming the same total feed rate. For instance, the energy required for a 5 wt % feed is about 1/5 of what is required for a 1 wt % ethanol in feed. Meaning, the steam needed is 1/5. This elevated temperature, 70° C. to 140° C., and pressure of 1.5 to 3.0 atm provide a thermodynamic driving force for the separation of ethanol from this stream. The recompressed vapor is sent to a membrane separation process, vapor permeation, where the ethanol is selectively removed, using an ethanol-selective membrane, and recovered in the permeate section of the membrane. The rejected stream containing, mostly, steam and $CO_2$ is then recycled to the fermentor to resume vapor generation.

The integrated MVR membrane separation process can produce an ethanol composition of at least 50 wt % ethanol from as low as 5 wt % ethanol in the feed (fermentation broth). The concentration of ethanol recovered in the permeate side of the membrane depends on the selectivity of the membrane. Suitable membranes include the majority of hydrophobic membranes, such as membranes made from hydrophobic polymers like polydimethylsiloxane (PDMS membranes), mixed matrix membranes (from hydrophobic polymers and zeolites, e.g., PDMS+ZSM5 membrane), and monolithic zeolite membranes from ZSM5 or silicalite. Vapor permeation and pervaporation based membrane separations using such membranes are well known and various groups are working on developing highly selective membrane materials for such applications. Suitable examples are as provided above. In some embodiments, the use of a highly selective hydrophobic membrane in vapor permeation mode is the preferred mode. The vapor generated should be of the quality (with very low or no foulants such as proteins, yeast, dissolved solids that would not damage the membrane element. Foulants concentrations below 500 ppm and preferably 50 ppm eliminate or reduce the need for a pretreatment before the membrane unit. Advantageously solids removal is handled in the fermentor by monitoring the ethanol concentration in the vapor which is dependent on the concentration of ethanol in the fermentor. The solid stream remaining in the fermentor is sent to the solids recovery or drying section after the ethanol in the broth is depleted to a satisfactory level.

The invention will be more particularly illustrated by referring to FIGS. 1 and 2. Those items which are the same in FIG. 2 as in FIG. 1 are numbered with the same numeral followed by the letter a. Additional elements for alternative embodiments are accordingly numbered in FIG. 2.

More specifically, a fermentor generally of size 100 gallons or larger such as 10,000 gallons, and up to 100,000 gallons is charged with, a fermentation source such as sugar, fermentable starch from biomass sources, grain, fermentable syngas from biomass, and the like. There after fermentation enhancing bacterium such as a thermo tolerant bacterium is added to the fermentor in an amount of sufficient to convert the biomass, etc to the production of ethanol. An aspect of this invention is the selection of a bacterium which can operate at higher temperatures than used in most fermentors. A suitable bacterium is described in Scopes R K, Volume 7, Number 4, 1997 pages 296-299. The mixture is heated to a temperature of about 80° C. to accelerate the fermentation process. The higher temperature of the fermentation enhances the volatility of the produced ethanol to permit the process of the invention to advance. Suitable examples are *Clostridium thermocellum*; *Clostridium thermohydrosulfurium*; *Geobacillus thermoglucosidasius*; *Thermoanaerobacter ethanolicus*; *Thermoanaerobacter finnii*; *Thermoanaerobacter mathranii*; *Thermoanaerobacterium saccharolyticum* and *Thermoanaerobacterium thermosaccharolyticum* and mixtures and combinations thereof.

After a suitable period of fermentation generally 1 to 250 hours or more, more preferably 5 to 50 hours, a gas such as $CO_2$ or nitrogen is introduced into the fermentor 100 through line 140. More particularly, the gas can be introduced into the fermentor once the fermentation process evidences a rise in the ethanol concentration, monitored by means known in the art. Therefore, one can begin the introduction of steam, $CO_2$, N2 at say 24 hrs, 48 hrs or as soon as one starts to notice ethanol concentration rising from initial reactor concentration. The introduction of the gas causes water-ethanol vapor to exit through the fermentor from the line 110 to be transferred to a compressor 120 for introduction into a membrane. The compressed vapor enters a membrane separation until 130 through line 122. The membrane is selected to pass the ethanol through and retain $CO_2$ and $H_2O$, Suitable membranes are zeolite and polydimethysiloxame (PDMS), and combinations thereof. The concentrated ethanol leaving the membrane separation unit 130 via line 200 may be further concentrated by methods known in the art. The higher the selectivity the better the separation. Selectivities as known in the art from 30 to 1000 can be employed. The retained $CO_2$ and $H_2O$ exits the membrane separation along path 130 where additional make up steam and/or $CO_2$ is added to the fermentor 100 as the process continues. During the fermentation process the solids will filter to the bottom of the fermentor and are removed along with purge water via line 170.

In an alternative embodiment illustrated in FIG. 2, unit 360 is used to separate $CO_2$ and $H_2O$ for disposal or recycle into the fermentor 100a via line 370.

A benefit of this process is the reduced amount of steam required (bulk of the steam entering the process is recycled) for ethanol recovery and thus reduced energy. Because the separation efficiency of the membrane process is not dependent on the volatility ratio of the components in the feed, steam is mainly used in this process to generate a vapor stream of ethanol in the feed to the MVR.

Figure 3:
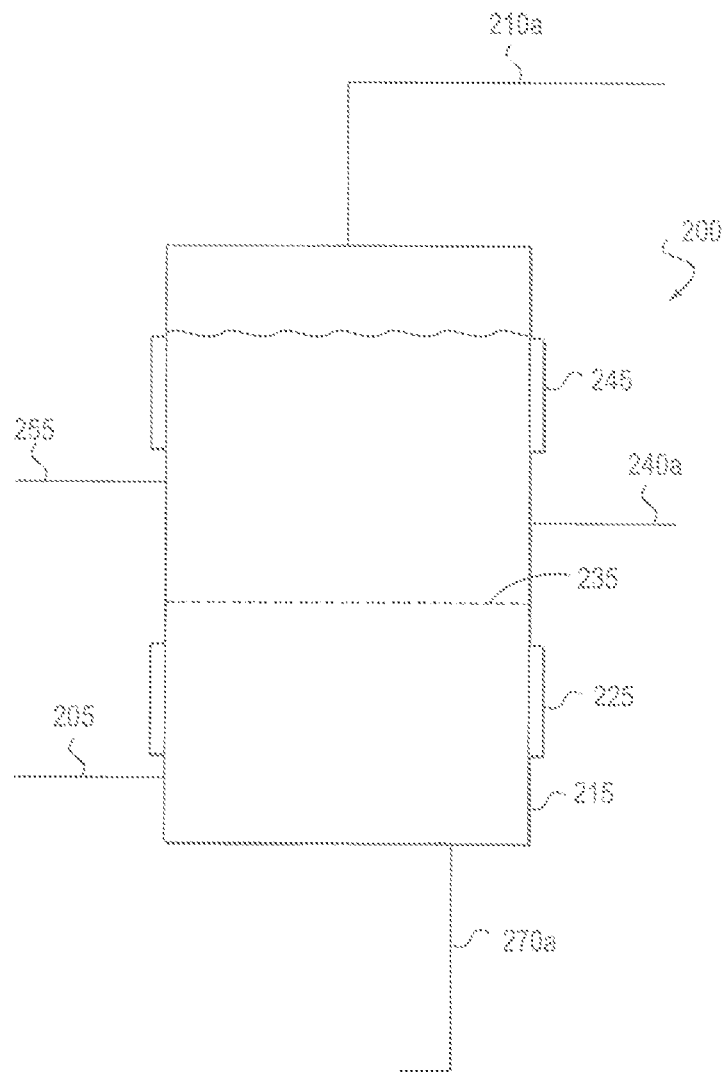
FIG. 3 illustrates a schematic of a reactor embodiment where the fermentations portion is maintained at a temperature lower than the region where the water/ethanol vapor mixture leaves the reactor.

Turning now to FIG. 3, an additional fermenting stripper is described. Fermentor/stripper 200 includes a tank portion 215 which can vary in size from 100 to 100,000 gallons with an inlet 205 to charge the biomass and fermenting mixture and bacterium. The fermentor/stripper 200 further includes the vapor exactor line 210a, which would pass the water ethanol vapor mixture to the compressor downstream thereof and a return line 240a which returns the concentrated $CO_2$ water mixture from the separator. Additionally the fermentor/ stripper 200 includes an exit line 270a for removal of solids and water and purging the system during cleaning operations. The fermentor 200 additionally includes means to maintain appropriate temperature, such as a heating bed (steam coil, etc.) 225 in the region of fermentor 200, in which the fermentation takes place. A screen 35 or other suitable filter lies above the heating bed 225 to keep the fermenting medium in the bottom of the fermentor, while passing the enriched water alcohol mixture to the top of the fermentor where an additional heating coil 245 raises the temperature of the mixture to 120° C. to 140° C. or higher to 180° C. Gas such as $CO_2$ and/or nitrogen is introduced via line 255 to accentuate the off gassing of the $H_2O$ and ethanol vapor.

The need for the thermal gradient created by elements 225 and 245 is reduced as the ethanologentic thermofiles are capable of operating at higher temperature and the circulation within the fermentor is such that the ethanol vapor is off gassed via line 210a, to maintain an ethanol concentration at the bottom of the reactor, such that the bacterium is not harmed. Concentrations of alcohol in the bottom of the fermentor are preferably kept below 5%. During operations, the fermentation process takes place at the bottom/lower section of the reactor, while the thermal gradient creates a circulation in which the ethanol-$H_2O$ vapor rises to the top where the gas assists in removing the ethanol/water vapor and then cools and sinks to the bottom of the reactor depleted in ethanol. Stirring mechanisms not illustrated, can help with the circulation.

EXAMPLE

The following example illustrates the operation of the process and apparatus of the invention.

A fermenting stripper, also referred to herein as a fermentor, is charged with as suitable medium of a biomass and methanol forming bacterium and heated to an excess of 120° C. at a pressure of 2 atm. The temperature is maintained with a steam coil within the fermenting stripper and the steam rate is about 87 pounds per hour. A water and ethanol $H_2O$ vapor exit the fermenting stripper at about 1 atmosphere and 99° C. at the rate of 112 pounds per hour which constitutes an 8.8 wt % ethanol-$H_2O$ mixture. This vapor is passed through a compressor, which compresses the ethanol water mixture to about 2 atm and raises the temperature to about 191° C. where upon it passed through an ethanolic separation membrane which separates the water and ethanol mixture. Ethanol exits the separation membrane and passes through a condenser. 99.9 wt % percent ethanol was recovered at a rate of about 10 pounds per hour. The $H_2O$ water-ethanol depleted mixture exits the membrane for recycling to the stripper at a pressure about 2 atm and a temperature of 121° C. at a rate 102 pounds per hour. This mixture is reduced in concentration of ethanol to about 0.05 wt %. In the process of exiting the compressor a return stream is fed to the fermenting stripper at pressure of 2 atm and temperature of 53° C. at a rate about 1,000 pounds per hour, having a 1 wt % ethanol concentration.

Modifications to the figures and the example within the skill of the ordinary artists are intended to be within the scope of the invention.

What is claimed is:

1. A fermentation process to recover ethanol which comprises:
   a. providing a fermentor capable of being charged with water, a fermentation enhancer and a source for the creation of the ethanol of the fermentation reaction;
   b. operating the fermentor at a temperature where the vapor pressure of the water-ethanol vapor phase mixture is sufficient to permit a membrane separator to concentrate the ethanol;
   c. flowing a gas into the fermentor to enhance the ethanol separation in the water-ethanol vapor phase;
   d. passing the water-ethanol vapor phase mixture through a compressor into a membrane separation unit;
   e. recovering ethanol from the membrane separation unit as the permeate;
   f. passing the stream reduced in ethanol back into the fermentor;
   g. and passing a water $CO_2$ stream through a membrane to separate $CO_2$ for recycle into the fermentor and a concentrated H2O stream for discharge or recycle into the fermentor.

2. The process according to claim 1 wherein the fermentor is operated from a temperature of about 75° C. to about 100° C.

3. The process of claim 2 wherein the fermentation enhancer is a bacterium is selected from the group consisting of *Clostridium thermocellum*; *Clostridium thermohydrosulfurium*; *Geobacillus thermoglucosidasius*; *Thermoanaerobacter ethanolicus*; *Thermoanaerobacter finnii*; *Thermoanaerobacter mathranii*; *Thermoanaerobacterium saccharolyticum* and *Thermoanaerobacterium thermosaccharolyticum*.

4. The process according to claim 1 wherein the product of Step C is passed through a compressor and into a membrane selected from the group consisting of hydrophobic polymers, mixed matrix membranes, and monolithic zeolite membranes.

5. An apparatus for the production of ethanol comprising:
   a fermentor capable of holding a source material for fermentation into ethanol, a fermentation catalyst to accelerate the formation of ethanol, and a suspending medium, said fermentor including an inlet for charging the fermentation materials to the fermentor, a vapor outlet capable of accepting an ethanol containing vapor, and a byproduct outlet capable of accepting solids and waste by products from the fermentation;
   a conduit connected to the vapor outlet in one end;
   a compressor connected to the conduit on the one end opposite thereto, said compressor having a low pressure inlet side connected to the conduit, and a higher pressure outlet side connected to a membrane separation unit;
   said membrane separation unit having an inlet to accept the pressurized stream from the compressor and capable of creating an ethanol concentrated stream for recovery and a stream depleted in ethanol to be recycled to the fermentor; and
   a unit attached to the fermentor by a conduit said unit capable of separating the fermentation solids broth into a $CO_2$ portion and a water disposal portion and/or a water recycle portion.

6. The apparatus according to claim 5 wherein the fermentor is from 100 to 100,000 gallons.

7. The apparatus according to claim 5 wherein the compressor is capable of compressing the water-ethanol vapor from a pressure of about 1 atm to a pressure of about 10 atm.

8. The apparatus according to claim 5 wherein the membrane is selected from a group consisting of zeolite; PDMS; and combinations thereof.

9. The apparatus according to claim 5 further including means to add fresh fermentation medium, catalyst, and water to the ethanol depleted recycle stream.

* * * * *